United States Patent [19]

Křovák et al.

[11] Patent Number: 4,683,062
[45] Date of Patent: Jul. 28, 1987

[54] METHOD OF CIRCULATION OF A LIQUID PHASE THROUGH A SOLID PHASE PARTICULARLY FOR BIOCATALYTICAL REACTIONS AND A DEVICE FOR REALIZATION THEREOF

[75] Inventors: Přemysl Křovák; Vladimír Běhůnek; Vladimír Vojtíšek; Miroslav Salvet; Pavel Hasal, all of Praque, Czechoslovakia

[73] Assignee: Ceskoslovenska akademie ved, Czechoslovakia

[21] Appl. No.: 803,815

[22] Filed: Dec. 2, 1985

[30] Foreign Application Priority Data

Nov. 30, 1984 [CS] Czechoslovakia ............ 9235-84
Jan. 23, 1985 [CS] Czechoslovakia ............ 449-85

[51] Int. Cl.$^4$ .................. C02F 3/06; C12M 1/16; C12M 1/18
[52] U.S. Cl. ............... 210/617; 210/150; 210/267; 210/256; 422/209; 422/211; 422/218; 435/299; 435/300
[58] Field of Search .............. 210/150, 151, 617, 267, 210/399, 780, 781, 784, 196, 256; 422/211, 218, 209; 435/299–301

[56] References Cited

U.S. PATENT DOCUMENTS

3,968,034 7/1976 Tymoszczuk .................. 210/275
4,594,228 6/1986 Lambert, Jr. et al. ............ 422/218

FOREIGN PATENT DOCUMENTS

780877 11/1980 U.S.S.R. .................. 210/267

Primary Examiner—Benoit Castel
Attorney, Agent, or Firm—Leydig, Voit & Mayer

[57] ABSTRACT

The method of circulation according to the invention consists in causing a part of the liquid part to rotate whereby centrifugal forces causes the rotating part of the liquid phase to form a rotating vortical liquid spindle that exerts a suction effect. The liquid to be circulated is then pumped into the spindle by suction, passes through a cavity destined for deposition of solid phase, said cavity being positioned in the space of the spindle, whereafter the liquid passes to the upper part of the spindle and is drawn back into a liquid phase container. The device for effecting this method of circulation consists of a vessel for liquid phase wherefrom the liquid phase is brought to a rotatable hollow body which incorporates a mantle, conveniently cylindrical, and a bottom which houses at least one opening for inlet of the liquid phase to the bottom of the body, or in some configurations a cover, said body being equipped by outlet openings for the exit of the liquid phase and having at least in its part at least one cavity for deposition and anchoring of solid phase, said cavity being provided in its part adjacent the axis of rotation or in its lower part with inlet openings for the liquid phase entering the cavity an incorporating in its part more distant from the axis of rotation or in its upper part outlet openings for the liquid phase leaving the cavity.

5 Claims, 4 Drawing Figures

METHOD OF CIRCULATION OF A LIQUID PHASE THROUGH A SOLID PHASE PARTICULARLY FOR BIOCATALYTICAL REACTIONS AND A DEVICE FOR REALIZATION THEREOF

BACKGROUND OF THE INVENTION

The invention concerns a method of circulation of a liquid phase through a solid phase, particularly for biocatalytical reactions performed for instance by means of immobilized enzymes and cells, and a device for realization thereof.

Some processes, particularly physical, chemical or biotechnological, require that a liquid should stream through a layer of porous, granular or similar material. It is known that layers of these materials substantially increase the area of contact between the liquid and the solid phase in the given volume of the appropriate device, thereby substantially accelerating the processes which arise as a consequence of interaction of the two phases.

Among the latter processes are physical adsorption, chemisorption, desorption, catalytical reactions (a carrier with an active layer), biocatalytical reactions, chromatography, ion exchange, etc.

Considerable importance has currently been gained by biological and biotechnological processes making use of the contact of a liquid phase with activated solid supports based on macroporous polymers and copolymers, hydrophilic pastes or gels, ion exchangers, which bear on their surfaces conjugated different biological materials.

In all these processes it is required that a liquid medium, for instance a fluid, should penetrate, leak, seep or stream through a layer of the solid support, during which process a desirable change occurs, usually an exchange or a change of some of the mass components between the fluid and the solid phase.

Biocatalysis is currently accomplished in a stirred batch reactor or in continuous reactors with stirred or fixed beds usually in columns. In both batch and continuous reactors the impeller is either anchor-shaped or paddle-wheel (screw-shaped or propeller-shaped paddles)

Biocatalysts are for the most part formed by amorphous (irregular) particles with size distribution 0.01 to 5 mm, and they are considerably damaged by the impact of the paddle-wheel agitators.

Continuous presence of biocatalyst particles in a stirred batch reactor is ensured for instance by a built-in filter septum at the bottom of the reactor above the outlet opening. After termination of the reaction the converted fluid is separated from the particles by filtration through said septum accomplished either by means of a vacuum (through the bottom of the reactor) or a pressure imposed on the surface of the fluid in the reactor. This filtration poses problems as it may cause clogging of the filter surface (pores in a textile material) and formation of a wet cake, and considerable pressure is necessary to remove the fluid from the reactor. Also, mechanical damage to the particles by the impeller during their repeated multiple use leads to the disintegration of larger particles to smaller ones which then clog the filter surface, limiting thereby its prolonged use.

DESCRIPTION OF THE PRIOR ART

A method and a device have been described for chemical reactions, particularly for peptide synthesis on insoluble supports by means of the reaction fluid (West German Pat. No. 2017351). The device consists of a reaction vessel for liquid medium and a reactor with permeable wall, which rotates underneath the surface of the liquid medium. Support particles are poured in bulk into the reactor. Due to the centrifugal force during the rotation of the reactor they form on the inner surface of the permeable reactor wall a layer the shape thereof, and thus also the liquid-solid interface, change in dependence on the magnitude of the centrifugal force, i.e. on the angular velocity of reactor rotation. The liquid medium penetrates through this layer and through the permeable reactor wall radially out of the reactor into the fluid external to the reactor, contained in the reaction vessel. The inlet of the liquid medium into the reactor which is completely immersed in the fluid is effected by an overflow of the fluid through a central opening in the upper cover of the reactor. This arrangement has the shortcoming that it does not permit the spraying of the fluid in the gaseous space above the fluid surface, i.e. it does not permit a concomitant aeration of the fluid which is required in some biochemical reactions, in particular in biocatalysis.

Moreover, various shaking or pulse-action devices, or devices in which the contact of the two phases is ensured by agitating the two phases by means of a gas, mechanical impellers of different types, nozzles, tube agitators, etc., have also been described. The shortcoming of, e.g., most paddle-wheel impeller systems, in which the solid phase (e.g. granules of macromolecular resins) is freely disposed in a rotating reactor, is the fact that a gradual erosion or abrasion of the supports or their disintegration takes place, decreasing thus the efficiency of the process.

Some of said shortcomings of the current systems are removed by the method of circulation of the liquid phase through the solid phase as constituted by the preseent invention. The invention consists in a method wherein a portion of the liquid phase is caused to rotate so that the centrifugal forces in the rotating liquid phase create a rotating vortical liquid spindle or its part, the central core of the spindle having the shape of a rotating liquid paraboloid or its part. Into the lower part of the vortical liquid spindle the circulating liquid phase is brought concomitantly and continuously by means of the sucking effect being created by the spindle. After transport by suction into the spindle the circulating liquid phase rises upwards along an ascending trajectory created inside the spindle, to the upper part of the spindle from where it is drawn off back into the liquid phase. The principle of the invention consists in the fact that solid phase is placed in the space occupied by the vortical liquid spindle in such a way that the liquid flowing through said spindle continuously circulates through this solid phase.

The described method of circulation is based on the fact that the liquid which occupies a part of a rotating, for instance cylindrical, vessel, will form a liquid spindle with a central core in the shape of an annular liquid paraboloid that exerts a sucking action, albeit only when further liquid is continuously brought to the lower part of the spindle and concomitantly drawn off from the upper part of the spindle, i.e. only under the condition of a circulation of liquid through the spindle.

A similar hydrodynamic principle forms the basis of a device described in Czechoslovak Pat. Nos. 228221, 228350, 231735, British Pat. No. 2,106 540 and others, except that these devices do not incorporate internally fixed solid phase but function merely as a paddle-less impeller, pump, etc.

SUMMARY OF THE INVENTION

According to the method described the liquid vortical spindle of said type is created e.g. by the rotation of a vessel shaped as a hollow vertical cylinder and filled partially with liquid phase, the vessel being equipped with a horizontal flat or dished bottom, the bottom having a central inlet opening for intake of liquid into the vessel. The vessel has no internal vanes and has relatively smooth inner walls. When the vessel is caused to rotate a vortical liquid spindle of a regular shape is formed within the vessel, the spindle exhibiting a suction effect in its lower part. The shape of the spindle can be affected by the shape of the vessel. The spindle need not always be annular in its whole shape, such as is formed by rotation of fluid and whose cross section is an annulus. Its shape can resemble only a part of the complete spindle form, e.g. a sector or a segment, depending entirely on the shape of the vessel. For instance, if the vessel with the liquid is shaped like a flat hollow rotating prism, centrifugal force will cause the formation of only a part of the "spindle" which will be U-shaped. The term "spindle" or its part should be conceived and comprehended also in this broader sense, analogously to the term liquid surface paraboloid.

The fact that the mentioned spindle has a suction effect makes possible pumping and circulation of the liquid phase through the "permeable" or "flow-through" solid phase or mass irrespective of the manner in which, or the place in the created spindle in which, the fluid phase is brought into the interior of the spindle. This enables the spindle to be formed not only below the surface and above the surface of the liquid phase but also apart from the liquid phase reservoir, for instance when the fluid for circulation is brought to the lower part of the spindle by a supply conduit from a distant supply tank, the transport of the fluid being ensured by the suction action of the spindle.

If it is desirable to obtain the longest possible trajectory of the streaming liquid in the spindle, the liquid should be brought to the spindle at the lowest possible point thereon. The vortical liquid spindle rotating at an angular rate about equal to that of the rotating vessel has the predominant function of a pump for fluid lifting.

The circulation of the liquid phase through the solid phase can be regulated and affected by the speed of revolution of the vessel in which the spindle is formed, by its size, dimensions, and locations of inlet and outlet openings whereby the liquid phase is brought into, or drawn off from, the vessel, by position of the rotation axis, change in the liquid flow rate through the vessel or the spindle, depth of immersion of the rotating vessel in the liquid phase, amount of the liquid phase in the vessel, etc. These factors affect also the shape of the spindle and its height including its central part (paraboloid) and the liquid flow rate in the spindle.

Another advantage of the fluid circulation according to the invention is the fact that if at high speed of revolution of the spindle in a rotating vessel the upper end thereof is covered by a cover, high hydrodynamic pressures are attained inside the spindle, said pressures permitting for instance a high flow of the liquid phase through a solid phase with a high flow resistance, or a high flow of highly viscous fluids through the solid phase, e.g. at high concentrations of substrates in the fluid.

The invention also concerns a device for performing the circulation according to the invention. The device consists of a container for the liquid phase from which said liquid phase is brought into a rotatable hollow body defined by a mantle and a bottom, said body being open at the top or being equipped with a cover and the bottom thereof having in places adjacent to the rotation axis at least one inlet opening for the liquid phases entering the rotatable hollow body, said body having in places more distant from the rotation axis at least one outlet opening for the liquid phase exiting from the rotatable hollow body. The principle of the device consists in the fact that at least in a part of the rotatable body at least one cavity is constructed for the deposition and anchoring of the solid phase, said cavity being fitted in its part adjacent to the rotation axis or in the lower part with inlet openings for the liquid phase entering the cavity and in its part more distant from the rotation axis or its upper part with outlet openings for the liquid phase leaving the cavity.

The cavity for deposition and anchoring of solid phase may contain flow-through or porous built-in structure of a replaceable construction for the solid phase.

Both the method and the device according to the invention are convenient in particular for catalytical reactions, adsorptions chemisorptions, desorptions, ion exchange, chromatography, biocatalytical reactions performed in particular by means of immobilized enzymes and cells, reactions on macromolecular carriers with active layer, etc.

The invention may also be used in various other fields of chemical engineering as it may perform concomitantly, or be adapted, as a paddle-less agitator or pump, liquid sprayer, defoaming device, filtration device, centrifuge, etc.

The term solid phase generally denotes material insoluble in the liquid and occurring in particles of different morphology, said particles being in contact with the liquid which can leak, seep or flow through this material.

In biotechnological devices the solid phase is usually represented by particles of immobilized enzymes or cells, the particles being loose, permeable or porous, amorphous, etc., and having the shape of granules, globules, platelets, filaments, scales, or being shaped into liners, plates or foils of porous or permeable character, or alternatively being provided in the art of compact nonporous materials with only their outer surface being enzymically active.

The solid phase or the built-in structures for retaining the solid phase and constructional components of said structures such as baffles on which the solid phase is fixed, need not always be porous. They may be in the art of layers (plates) generally impermeable to the fluid but provided with channels or gaps between individual plates, the mentioned gas or channels providing means for streaming or circulating of the liquid caused by centrifugal forces, or at least for maintaining contact between the liquid and the surface of the plates. On the other hand, the "solid phase" can be constituted by a substance of a paste-like, geletinous or similar consistency or by any other matter through which the liquid phase can pass.

The liquid phase denotes in particular liquids and fluids, Newtonian and non-Newtonian, i.e. highly viscous, which still "flow" in a gravitational or centrifugal field, and also gases alone or in combination with liquid phase, etc.

The hollow rotatable body can have different shapes which can be symmetric or asymmetric in relation to the axis of rotation. The axis of rotation can have different position or direction. Also, the shape and number of cavities for deposition and anchoring of the solid phase, their disposition (central or excentric) or direction and distribution of inlet and outlet openings in these cavities are not decisive.

In some cases the volume of the solid phase in the rotatable body should be as large as possible in relation to the size of this rotatable body. In this case the body conveniently be shaped as a vertical hollow cylinder with a horizontal flat or slightly dished bottom, with a central inlet opening in the bottom, and the cavity with the solid phase should have the same or a similar shape, location and dimensions as the liquid spindle or annulus at given rotation. An annular built-in structure of the solid phase container, simulating the shape of the spindle, has the additional advantage that the spindle has a regular shape and the hydrodynamic losses are small (low turbulence, etc.). Also, the construction can be such that the rotatable hollow body contains a multitude of separate cavities mutually disconnected and in different positions, each of said cavities enclosing solid phase in such a way that no free mutual movement of the particles takes place. Each of these cavities can enclose a different type of solid phase (different shape, filler composition, etc.).

The rotatable hollow body can also be provided with cavities, spaces, parts or components destined for purposes other than the containment and fixation of solid phase.

One of the convenient variants of the device according to the invention is embodied in a hollow rotatable body partially immersed below the surface of the liquid phase, said body having a cylindrical mantle and having also a bottom provided with a central inlet opening for the intake of the liquid phase into the hollow rotatable body, the body having in the peripheral circumferential part of its cover or in the upper part of the mantle outlet openings for the exit of the fluid from the rotatable hollow body.

The cylindrical shape of the hollow body, the inner walls whereof are smooth, is convenient because of the low hydrodynamic resistance which arises during the formation of the liquid spindle inside the body, the low resistance rendering the process energetically advantageous.

The hollow rotatable body is thus entirely or in part submerged below the surface of the liquid phase. The interior of the rotatable body is fitted with one or more cavities for deposition and anchoring of the solid phase, said cavities being provided with inlet openings for the entry of the liquid phase into the cavity in its part nearer to the axis of rotation, and with outlet openings for the exit of the liquid phase from the cavity in its part more distant from the axis of rotation.

The inlet and outlet openings in the cavity are fashioned so as to enable the liquid phase to flow through the solid phase secured in the cavity, said flow being caused by centrifugal forces.

In some cases the liquid phase passes through the solid phase radially or horizontally. This situation arises if, e.g., the rotatable body embodies two concentric perforated mantles between which the cavity for deposition and anchoring of the solid phase is formed.

In other cases it is desirable that the liquid phase should flow through the solid phase in directions other than horizontal (radial), for example in an upward direction (at an angle, spirally, vertically). In these configurations it is convenient that the inlet openings for the liquid phase should be placed, e.g., in the lower horizontal part or the side part of the cavity securing the solid phase, and analogously the outlet openings for the liquid phase should be in the upper horizontal part or the side part of the cavity containing the solid phase.

The flow of liquid from the hollow rotating body, that takes place after the liquid has left the cavity containing the solid phase, can occur, e.g., over the top edge of the rotatable body if the mentioned body is without a cover (in particular of this part of the rotatable body protrudes above the surface of the liquid phase) or if the body is fitted with a cover said cover having in its peripheral circumferential part outlet openings, or similar openings being situated in the upper part of the mantle of the rotatable body.

The cavities for securing and anchoring of the solid phase, situated in the rotating body, can also contain replaceable flow-through or porous built-in elements for retaining the solid phase. The built-in structure can be represented by a mere frame or skeleton produced with grooves or notches for securing of the solid phase, etc.

The built-in structure is usually fixed to the rotable hollow body and rotates with it.

The said built-in structure can contain the independent axis of rotation and owing to this fact the independent process of the rotation of this built-in structure can exist also.

There exist more possibilities: the built-in structure rotates with another angular velocity than the rotable hollow body, or it rotates in the oppositie direction than the hollow body, it does not rotates etc.

In devices for biocatalytical reactions or immobilized enzymes or cells, the rotatable body can conveniently have the shape of two concentric perforated mantles, particularly cylindrical or fructoconical, the inner mantle having inlet openings for liquid medium. This configuration provides between the two mantles a space where the biocatalyst particles are secured. The perforated inner or outer mantle can have means to attach to its surface a netting or webbing shroud, conveniently from a textile material, with mesh smaller than the dimensions of the solid phase particles. The inlet openings in the inner mantle can be situated directly opposite the outlet openings in the outer mantle of the rotating body.

BRIEF DESCRIPTION OF THE DRAWING

The accompanying drawing shows in front view examples of devices for the contact of a solid and a liquid phase in a centrifugal field according to the invention.

In all instances (FIGS. 1 through 4) the drawings illustrate only one variant of the device, in which the hollow rotatable body has a cylindrical or frustoconical mantle with a vertical shaft, with a central circular inlet opening in the bottom of the body, said bottom being horizontal and the cavity for securing the solid phase inside the body having the shape of a complete annulus. In these cases the volume of the solid phase relative to the volume of the whole rotating body can be maximal, the spindle can have a symmetric shape and can form a complete annulus, not only its part, and the hydrodynamic losses caused by turbulence can be minimized.

DESCRIPTION OF THE PREFERRED EMBODIMENTS

Figures 1, 2:
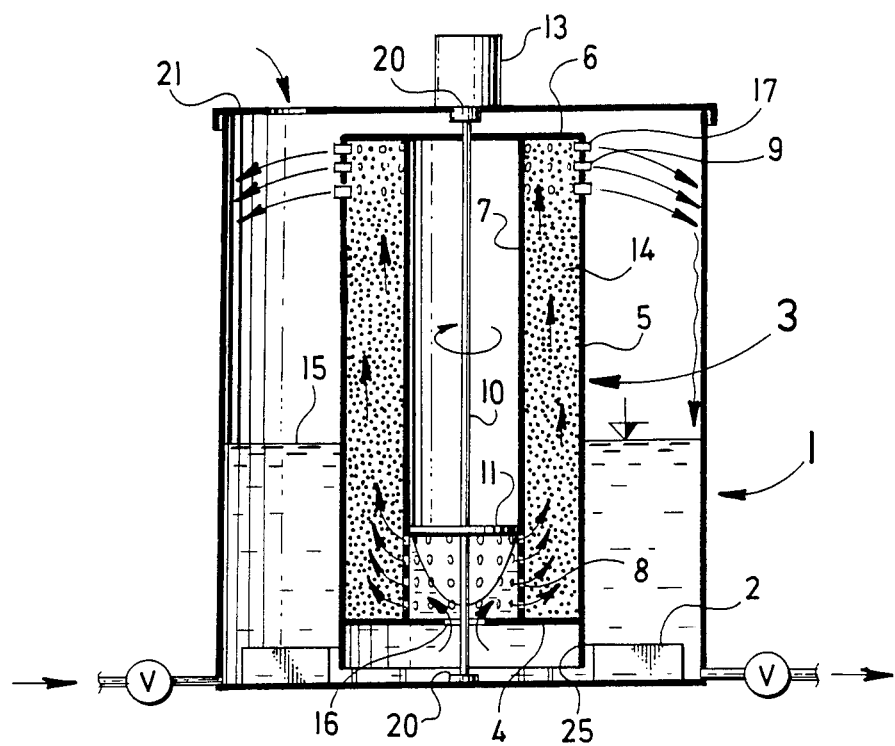
FIG. 1 shows a hollow rotating body (a rotor) with an outer and an inner mantle and with solid phase secured in the gap between the two mantles. The upper part of the rotor, which houses outlet openings, protrudes above the surface of the liquid in the reaction vessel (spraying of the liquid above the surface).
FIG. 2 shows a device according to the invention in which the rotor cavity contains built-in structure in the form of chambers with perforated vertical or horizontal walls, the mentioned chambers enclosing the solid phase. The exit of the liquid from the rotor over the upper edge thereof is effected at the height of the liquid phase surface.

FIG. 1 shows in front view one alternative of the device for the contact of solid and liquid phase according to the invention.

The device embodies a reaction vessel 1 for the liquid phase 15, with a lid 21 and baffles 2. Partially immersed in the vessel is a hollow rotor 3 of a cylindrical shape with a vertical driving shaft 10 driven by electric engine 13 equipped with means for regulating revolutions, said shaft 10 passing through bearing 20 in the lid 21 of the vessel 1.

The hollow rotor 3 consists of an outer mantle 5, removable cover 6 and a bottom 4 which has a central opening 16 for the inlet of the fluid phase 15 to the bottom 4 of the hollow rotor 3. The outer mantle 5 of the rotor 3 has in its upper part outlet openings 17 arranged in rows above each other, some of said openings being fitted with nozzles 19.

Inside the rotor 3 is an inner mantle 7 of tubular shape, with inlet openings 8 in the lower part of the mantle 7. The cavity between the inner mantle 7 and the inner wall of mantle 5 of the rotor 3 is filled with the solid phase 14 (reaction agent).

The hollow rotor 3 with a tubular extension 25 is immersed by its lower part (bottom) in the liquid phase 15 in such a way that the upper part of rotor 3 and thus of the mantle 5 with the outlet openings 17 protrudes above the surface of the liquid phase 15. Shaft 10 is attached to the inner mantle 7 by means of a strut 11 and its opposite end is rotatably mounted in the bottom of the reaction vessel 1 in a bearing 20.

As soon as the rotor 3 begins to rotate in vessel 1 at a sufficient angular velocity the centrifugal forces cause the liquid inside the rotor 3 to form a vortical liquid spindle in the centre whereof an annular liquid paraboloid is formed. The diameter of solid granules 14 does not exceed the diameter of the outlet openings 17 or nozzles 19 in the upper part of the outer mantle 5 of rotor 3. The height of the liquid paraboloid changes with changing angular velocity. The suction effect of the liquid vortical spindle causes the liquid phase 15 to be first pumped inside through the inlet opening 16, and to be transported to the bottom 4 of the rotor 3 through the tubular extension 25 which makes posssible an increased flow through the rotor 3 and, in terms of the flow, precedes the opening 16. Through openings 8 in the lower part of the inner mantle 7 the liquid phase 15 streams along a spiral ascending trajectory through the solid phase 14 which is deposited in the cavity between the inner mantle 7 and the inner wall of the mantle 5. In the upper part of mantle 5 carrying outlet openings 17 or nozzles 9 the liquid phase 15 leaves the rotor 3 and is sprayed fan-like in the space above the liquid surface and returns then in droplets in free fall back to the liquid phase 15, which in this manner circulates in reaction vessel 1.

As the rotor 3 is equipped on its upper end with a cover 6 then with increasing velocity of rotation the centrifugal force in the liquid streaming inside the rotor 3 increases together with the velocity of the liquid including its outflow velocity from outlet openings 17 or nozzles 9.

The space above the surface is filled with air (or another gas) which is continuously recirculated, thus ensuring aeration of the liquid phase 15 which is desirable for reactions such as aerobic fermentation or biocatalysis.

Another alternative device according to the invention is depicted in front view in FIG. 2. It differs from the preceding one illustrated in FIG. 1 in that the solid phase 14 fills a built-in structure 22 shaped as an annulus, said annulus having a height lower than the height of the mantle 5 of rotor 3. The cavity with the built-in means 22 is closed at the upper end by a lid 18 with outlet openings 27 and at the lower end by a bottom 19 with inlet openings 8. Shaft 10 driven by electric engine 13 is rotatably mounted in a supporting frame 28 in bearing 20. Rotor 3 has no cover 6 so that the liquid phase 15, after passing through the whole column 5, leaves the rotor 3 directly by being carried over the upper edge of said reactor in the shape of a liquid annulus back on the level of the liquid phase external to the rotor. The built-in structure 22 which is replaceable, consists of perforated vertical and horizontal plates (walls) arranged so as to form independent hollow chambers 23, said chambers constituting a supporting skeleton of the built-in means 22. The built-in structure 22 can be removed from the rotor 3 and replenished with reaction agent which has the consistence of, e.g., porous paste or semipaste. The function is similar as in device according to FIG. 1.

The liquid phase 15 from container 26 is brought to the bottom 4 of the rotating rotor 3 and then ascends gradually into separate chambers 23 of the built-in structure 22. The liquid medium flowe under the action of centrifugal force through these chambers 23 filled with the solid phase 14 and through the outlet openings 27 in the lid 18 and over the upper edge of the rotor 3 to the surface of liquid in container 26 where it is dispersed on the surface in a thin layer.

This configuration is convenient for, e.g., treatment of waste waters in ponds or reservoirs, particularly in a continuous flow-through arrangement.

Figure 3:
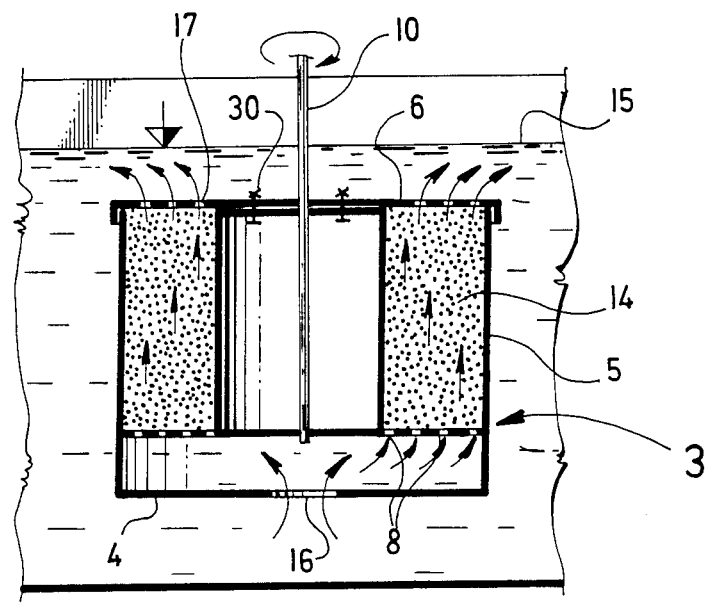
FIG. 3 illustrates a device according to the invention which rotates below the surface of the liquid phase and contains a cavity for securing and anchoring of the solid phase, said cavity having inlet and outlet openings in the lower and upper horizontal cavity walls.

FIG. 3 illustrates in a front view another variant of the device according to the invention. It consists of a cylindrical hollow rotor 3 which rotates completely submerged below the surface of the liquid phase 15 confined in a reaction vessel 1. The bottom 4 of rotor 3 is fitted with a central inlet opening 16. The cavity has annular shape and is packed with solid phase 14 and covered by a cover 6. Inlet openings 8 are arranged in the lower horizontal wall of the cavity whereas the upper horizontal wall of the cavity contains outlet openings 17.

Figure 4:
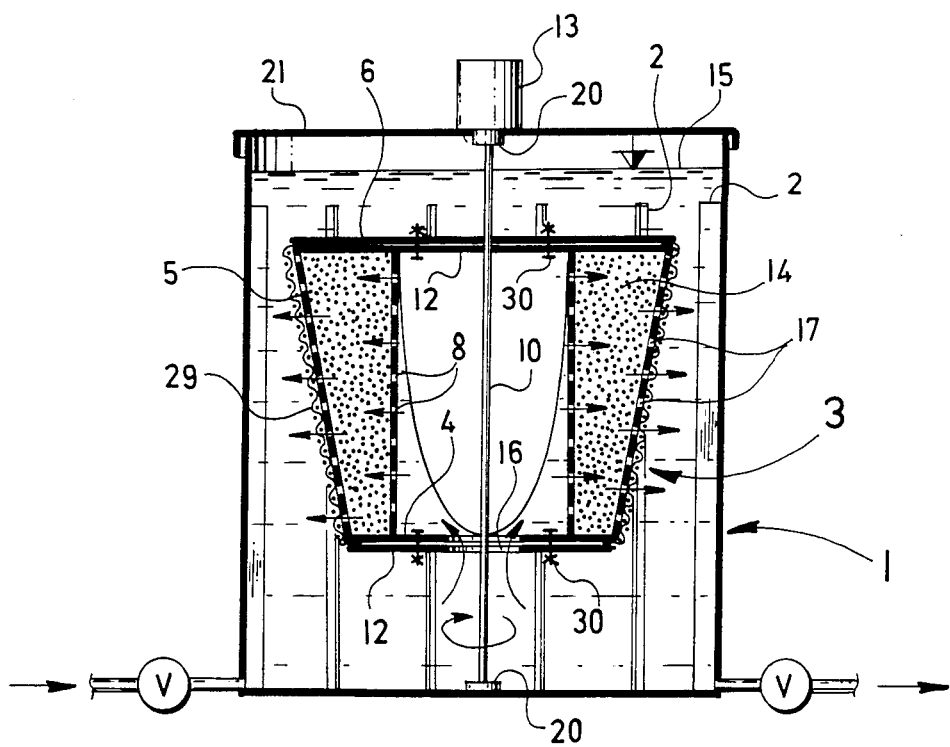
FIG. 4 shows a device convenient particularly for biocatalytical reactions by means of immobilized enzymes and cells, with a radial inflow and outflow of the liquid from the cavity containing the solid phase.

FIG. 4 shows the front view of another type of the device according to the invention. The device consists of a reaction vessel 1 filled with a liquid reaction medium. The vessel contains four baffles 2 in the shape of vertical bars, said baffles preventing the formation of a central vortex in vessel 1.

Vessel 1 is equipped with a lid 21 on which is mounted electric engine 13 with a shaft 10 connected with a hollow rotor 3 which is completely immersed in the liquid reaction medium. The lower part of shaft 10 is anchored in the bottom of vessel 1. The hollow rotor 3 consists of a bottom 4 with a central inlet opening 16, of a cover 6 and of two concentric perforated mantles—an outer mantle 5 with outlet openings 17 and an inner mantle 7 with inlet openings 8.

The inner mantle 7 has cylindrical shape whereas the outer mantle 5 has a frustoconical shape. The outer conical mantle 5 has attached thereon a netting shroud 29 fabricated from a nylon flour cloth. The shroud 29 is attached to the cover 6 and to the bottom 4 of the hollow rotor 3 by means of an upper and a lower flange 12 with connection screw 30.

Between mantles 5 and 7 is an annular cavity containing particles 14 of immobilized cell catalysts.

The body of the hollow rotor 3 can be disassembled to individual parts which can thus be replaced when necessary (a building-block system).

The rotating rotor 3 with the biocatalyst is completely submerged below the surface of the medium. The liquid reaction medium is pumped by suction into the central inlet opening 16 in the centre of the bottom 4 to rotor bottom 4. From there the liquid medium is lifted upwards along the wall of the inner mantle 17, said medium passing through a spiral trajectory to the shape of a spindle.

The centrifugal force causes the liquid medium to pass gradually through the biocatalyst particles 14 packed in the space between the two mantles, 5 and 7, achieving thereby a cyclic interaction of the catalyst with the liquid medium and thus a biochemical reaction.

The centrifugal forces cause a continuous outflow of the liquid reaction medium from the hollow rotor 3 through outlet openings 17 in the outer mantle 5 back into the liquid medium.

When the reaction ability of the liquid medium has been exhausted the liquid product is drained off, the reaction vessel is filled with new reaction medium and the whole process is repeated with the same biocatalyst and in the same device.

Devices according to FIGS. 3 and 4 can be used particularly for biocatalytical reactions, biotransformations and bioconversions of substrates to desired products, either by multiple repetition of the process or continuously, in particular for hydrolysis, addition of different groups, isomerization, racemization, optical resolution, oxidoreduction, decarboxylation, groups transfer and exchange, etc.

The manner and the device according to the invention are suitable expecially for catalytic reactions, adsorptions, chemisorptions, desorptions, ion exchange, chromatography, biocatalytical reactions performed in particular by means of immobilized enzymes and cells, reactions on macromolecular carriers with active layer, etc.

The invention can also be used in various other fields of chemical engineering insofar as it can perform, or be adapted, concomitantly as a paddle-less agitator or pump, liquid sprayer, defoaming device, filtration device, centrifuge, etc.

We claim:

1. A method for the circulation of a liquid phase through a solid phase, comprising: rotating a part of the liquid phase so that centrifugal forces induce the rotating fluid to form at least a part of a rotating vertical liquid spindle, the spindle having an upper part, a lower part, and a central core, the central core of said spindle having the shape of at least a part of a liquid surface paraboloid, continuously supplying the lower part of said vertical liquid spindle with circulating liquid phase as a result of suction exerted by the rotating spindle, allowing said liquid phase to ascend along an upward-directed trajectory created inside the spindle to the upper part of said spindle, and allowing said liquid phase while ascending to also pass through a solid phase which is located along the upward-directed trajectory created inside said spindle, and allowing the liquid phase, after reaching the upper part of said spindle, to be drawn back into the liquid phase.

2. A device for the circulation of a liquid phase through a solid phase, comprising: a vessel for holding a liquid phase, a rotatable hollow body located within said vessel for the circulation of said liquid phase, said hollow body being formed by a mantle and a bottom, said bottom having adjacent the axis of rotation at least one inlet opening for the liquid phase to enter the hollow rotatable body, said hollow rotatable body also having distant from the axis of rotation at least one outlet opening for the liquid phase to exit from the hollow rotatable body, and means for rotating said hollow body, said device further comprising at least one cavity for depositing and anchoring a solid phase, said cavity being located within at least a part of the rotatable body and having inlet openings (8) for the liquid phase to enter the cavity and outlet openings (17) for the liquid phase to leave the cavity.

3. A device according to claim 2 in which the cavity is realized by two concentric perforated mantles (5, 7) conveniently shaped like cylinders or truncated cones, and comprising an inner mantle (7) with inlet openings (8) and an outer mantle (5) with outlet openings (17) for the liquid phase, the space between the two mantles (5, 7) containing at least one cavity for the deposition of solid phase.

4. A device according to claim 2, wherein the cavity is equipped with a flow-through or porous replaceable built-in structure (22) for the solid phase filling.

5. A device according to claim 3, wherein the cavity is equipped with a flow-through or porous replaceable built-in structure (22) for the solid phase filling.

* * * * *